(12) United States Patent
Oota

(10) Patent No.: US 6,508,586 B2
(45) Date of Patent: Jan. 21, 2003

(54) IVR-CT APPARATUS

(75) Inventor: Satoshi Oota, Imaichi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 09/964,582

(22) Filed: Sep. 28, 2001

(65) Prior Publication Data

US 2002/0039403 A1 Apr. 4, 2002

(30) Foreign Application Priority Data

Sep. 29, 2000 (JP) ......................................... 2000-298674

(51) Int. Cl.[7] ................................................. H05G 1/02
(52) U.S. Cl. .......................... 378/196; 378/195; 378/194
(58) Field of Search ............................. 378/4, 195, 196, 378/198, 197, 193, 20

(56) References Cited

U.S. PATENT DOCUMENTS 6,435,713 B1 * 8/2002 Iizuka ........................... 378/195

* cited by examiner

Primary Examiner—David P. Porta
Assistant Examiner—Courtney Thomas
(74) Attorney, Agent, or Firm—Oblon, Spivak, McClelland, Maier & Neustadt, P.C.

(57) ABSTRACT

An IVR-CT apparatus of the present invention includes a bed including a table top movable in its longitudinal direction, an X-ray diagnostic apparatus including an arm movably placed in the vicinity of the bed, an X-ray CT apparatus including a CT gantry movably placed in the vicinity of the bed, a position memory for storing a plurality of position data sets containing position data of the arm and position data of the CT gantry, a control panel including a plurality of positioning switches for selecting an arbitrary one of the plurality of position data sets, and a controller for controlling the movements of the arm and the movements of the CT gantry in accordance with the selected position data set.

15 Claims, 12 Drawing Sheets

| HEAD STANDARD POSITION | | | |
|---|---|---|---|
| CT GANTRY POSITION | :±XXmm | C-SHAPED ARM STRUT-ROTATION ANGLE | :±XX° |
| CT GANTRY TILT ANGLE | :±XX° | C-SHAPED ARM TILT ANGLE | :±XX° |
| | | C-SHAPED ARM SLIDE-ROTATION ANGLE | :±XX° |
| TABLE TOP HEIGHT | :XXcm | SIDE POSITION | :±XXmm |
| TABLE TOP POSITION | :±XXmm | C-SHAPED ARM LONGITUDINAL POSITION | :±XXmm |
| | | SID | :XXmm |

FIG. 9A

| HEAD STANDARD POSITION | | | |
|---|---|---|---|
| CT GANTRY POSITION | :±XXmm | C-SHAPED ARM STRUT-ROTATION ANGLE | :±XX° |
| CT GANTRY TILT ANGLE | :±XX° | C-SHAPED ARM TILT ANGLE | :±XX° |
| | | C-SHAPED ARM SLIDE-ROTATION ANGLE | :±XX° |
| TABLE TOP HEIGHT | :XXcm | SIDE POSITION | :±XXmm |
| TABLE TOP POSITION | :±XXmm | C-SHAPED ARM LONGITUDINAL POSITION | :±XXmm |
| | | SID | :XXmm |

FIG. 9B

| HEAD STANDARD POSITION | | | |
|---|---|---|---|
| CT GANTRY POSITION | :±XXmm | C-SHAPED ARM STRUT-ROTATION ANGLE | :±XX° |
| CT GANTRY TILT ANGLE | :±XX° | C-SHAPED ARM TILT ANGLE | :±XX° |
| | | C-SHAPED ARM SLIDE-ROTATION ANGLE | :±XX° |
| TABLE TOP HEIGHT | :XXcm | SIDE POSITION | :±XXmm |
| TABLE TOP POSITION | :±XXmm | C-SHAPED ARM LONGITUDINAL POSITION | :±XXmm |
| | | SID | :XXmm |

FIG. 9C

| HEAD STANDARD POSITION | | | |
|---|---|---|---|
| CT GANTRY POSITION | :±XXmm | C-SHAPED ARM STRUT-ROTATION ANGLE | :±XX° |
| CT GANTRY TILT ANGLE | :±XX° | C-SHAPED ARM TILT ANGLE | :±XX° |
| | | C-SHAPED ARM SLIDE-ROTATION ANGLE | :±XX° |
| TABLE TOP HEIGHT | :XXcm | SIDE POSITION | :±XXmm |
| TABLE TOP POSITION | :±XXmm | C-SHAPED ARM LONGITUDINAL POSITION | :±XXmm |
| | | SID | :XXmm |

FIG. 9D

IVR-CT APPARATUS

CROSS-REFERENCE TO RELATED APPLICATIONS

This application is based upon and claims the benefit of priority from the prior Japanese Patent Application No. 2000-298674, filed Sep. 29, 2000, the entire contents of which are incorporated herein by reference.

BACKGROUND OF THE INVENTION

1. Field of the Invention

The present invention relates to an IVR-CT apparatus (interventional radiology-computed tomography apparatus)

2. Description of the Related Art

An IVR-CT operation means an operation such as blood vessel formation by catheter manipulation on the basis of X-ray imaging/fluoroscopy of planar images and CT imaging/fluoroscopy of tomographic images. An IVR-CT apparatus is designed for this IVR-CT operation. That is, in a blood vessel imaging room having equipment equivalent to an operation room, an X-ray computer tomographic apparatus (X-ray CT apparatus) is installed together with a circulatory organ X-ray diagnostic apparatus (also called an angiographic apparatus) including a catheter bed. In this IVR-CT apparatus, an operator can check the planar position of a catheter by a planar image and can check the sectional position of the catheter by a tomographic image. Accordingly, the operator can accurately recognize the present position of the catheter and accurately determine the advancing direction.

Unfortunately, the conventional IVR-CT apparatus has the following problem. The catheter bed has a control panel for controlling the up/down movement and longitudinal movement of a table top. A C-shaped arm has a control panel for controlling the strut rotation, slide rotation, tilt, longitudinal movement, side movement, and SID adjustment of the arm. Also, the housing of a CT gantry has a control panel for controlling the tilt angle and front/rear movement of the gantry. By using these control panels, an operator can freely position the table top, C-shaped arm, and CT gantry.

These three control panels, however, are placed physically separated from each other. Therefore, a doctor or an assistant such as a nurse who assists the doctor must go and return between the three control panels, and this lowers the operability. For example, when CT fluoroscopy is to be executed subsequently to X-ray fluoroscopy, an operator starts from the home position, moves along the C-shaped arm control panel, the CT gantry control panel, and the bed table side control panel, and then returns to the home position.

BRIEF SUMMARY OF THE INVENTION

It is an object of the present invention to improve the operability of the positioning of a bed, C-shaped arm, and CT gantry in an IVR-CT apparatus.

According to an aspect of the present invention an IVR-CT apparatus comprises a bed including a table top movable in a longitudinal direction thereof, an X-ray diagnostic apparatus including an arm movably placed in the vicinity of the bed, an X-ray CT apparatus including a CT gantry movably placed in the vicinity of the bed, a position memory for storing a plurality of position data sets containing position data of the arm and position data of the CT gantry, a control panel including a plurality of positioning switches for selecting an arbitrary one of the plurality of position data sets, and a controller configured to control the movements of the arm and the movements of the CT gantry in accordance with the selected position data set.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention and, together with the generation description given above and the detailed description of the embodiments given below, serve to explain the principles of the invention.

FIG. 9A is a view showing an example of a head standard position displayed on a display panel shown in FIG. 1;

FIG. 9B is a view showing an example of an abdomen standard position displayed on the display panel shown in FIG. 1;

FIG. 9C is a view showing an example of a park position displayed on the display panel shown in FIG. 1;

FIG. 9D is a view showing an example of a given position number and position data corresponding to the position number displayed on the display panel shown in FIG. 1;

DETAILED DESCRIPTION OF THE INVENTION

Figure 1:
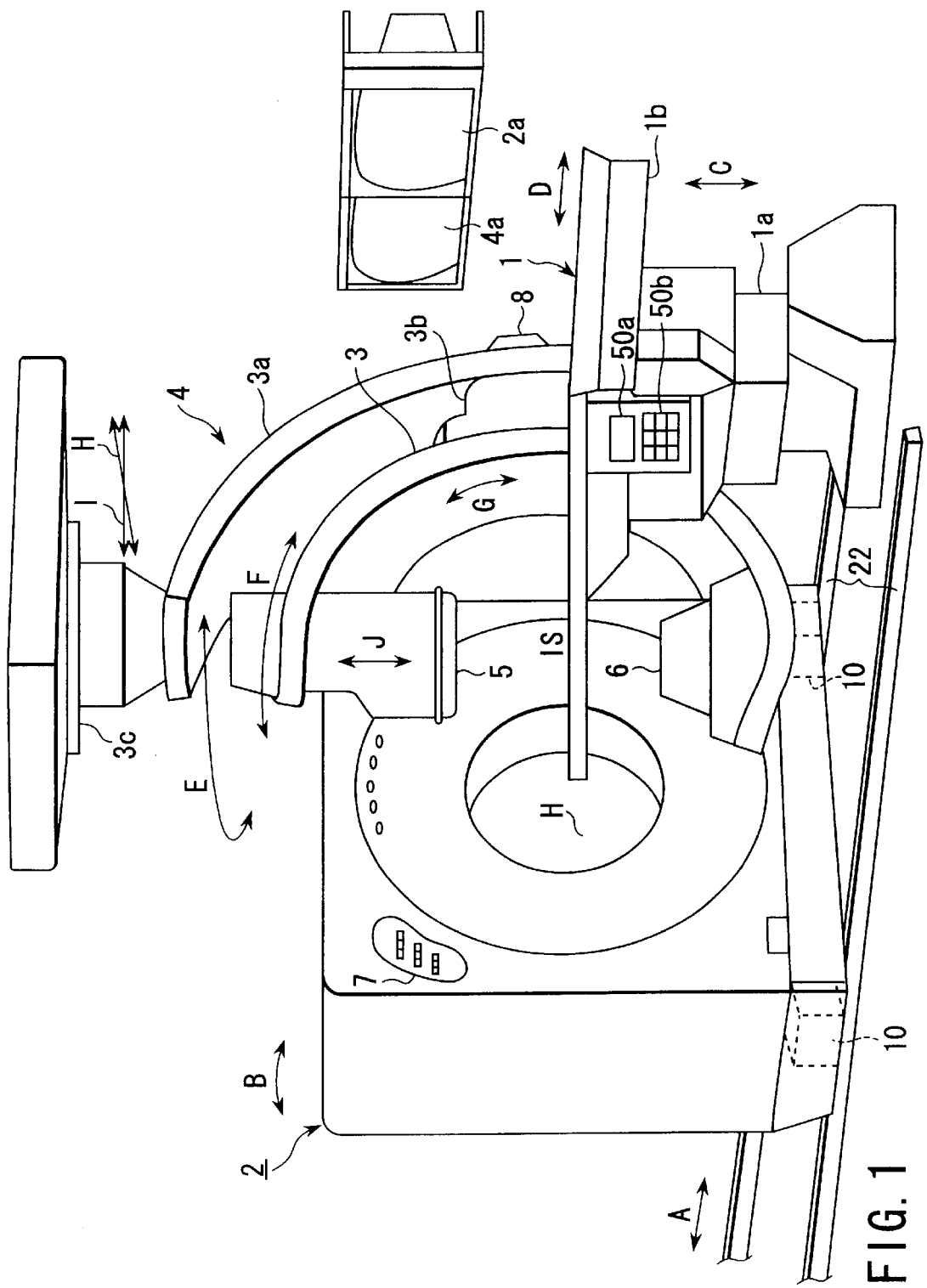
FIG. 1 is an external view of an IVR-CT apparatus according to an embodiment.
Figure 2:
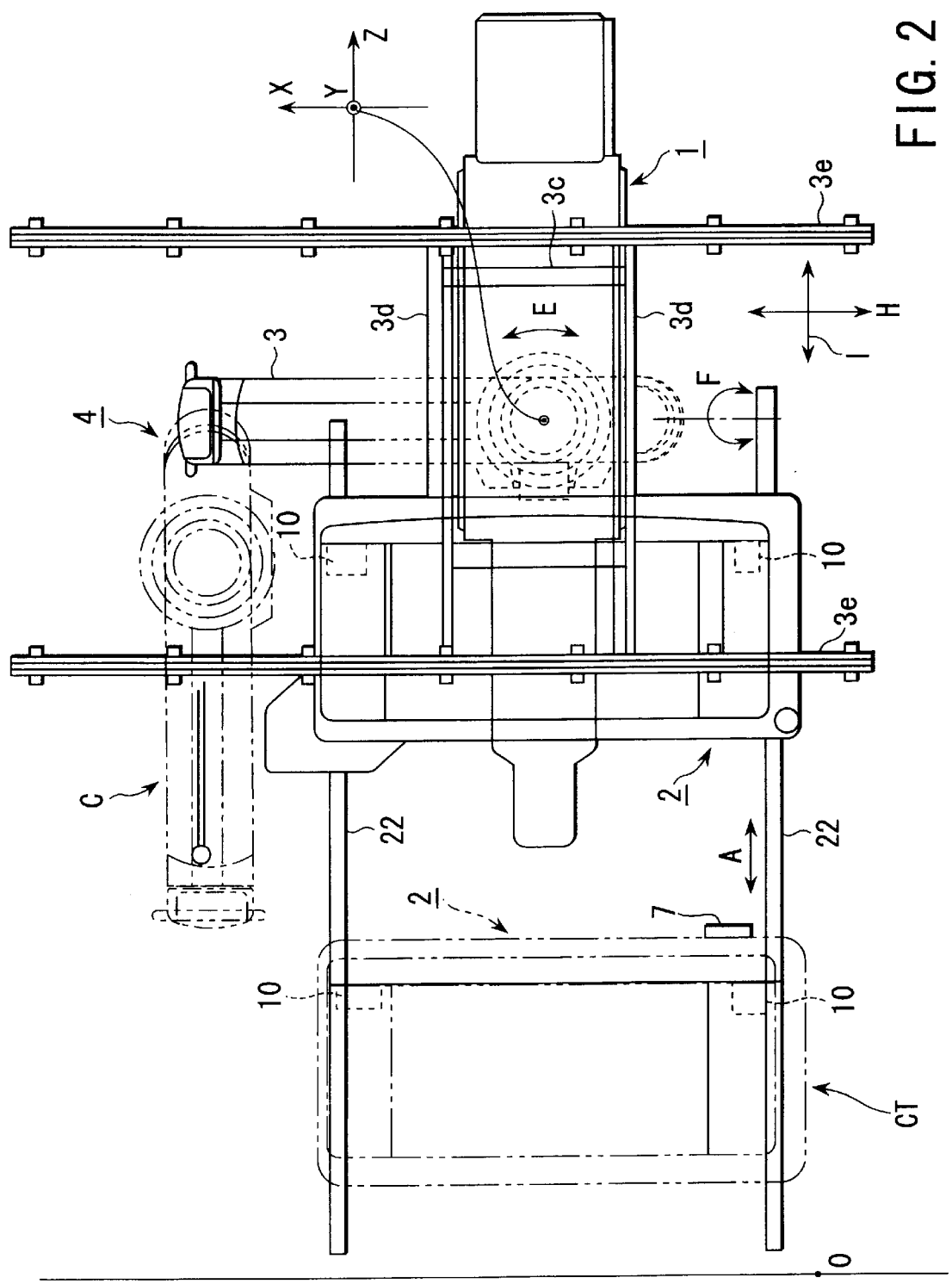
FIG. 2 is a plan view of the IVR-CT apparatus shown in FIG. 1.
Figure 3:
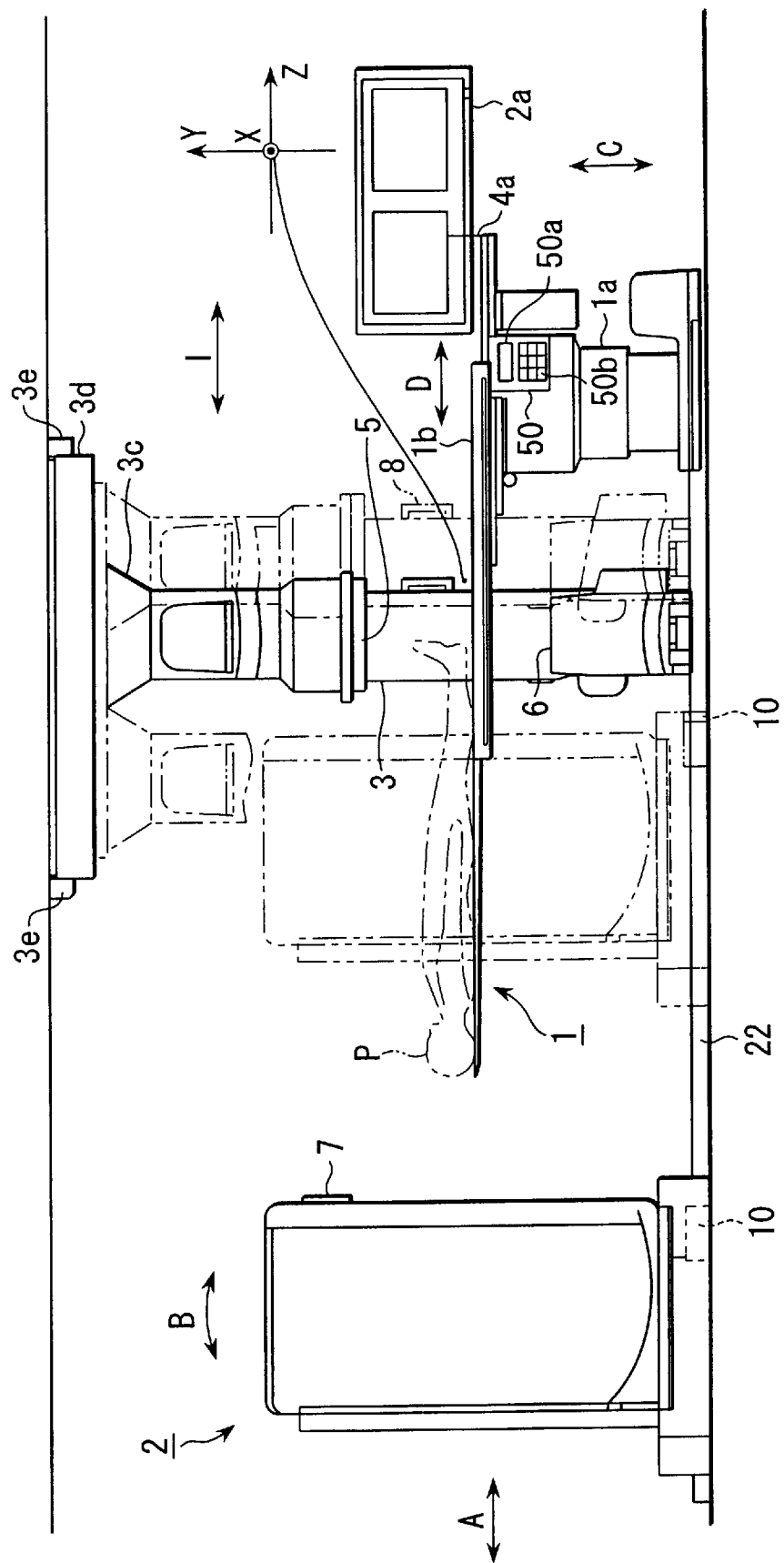
FIG. 3 is a side view of the IVR-CT apparatus shown in FIG. 1.

An embodiment of the present invention will be described below with reference to the accompanying drawing. FIG. 1 is an external view of an IVR-CT apparatus according to this embodiment. FIGS. 2 and 3 are plan and side views, respectively, of the apparatus.

This IVR-CT apparatus includes a circulatory organ X-ray diagnostic apparatus (angiographic apparatus) 4 which includes a catheter bed 1 and a substantially C-shaped (or U-shaped) support member (to be referred to as "C-shaped arm" hereinafter) 3, and an X-ray CT apparatus which includes a CT gantry 2. The catheter bed 1 has a table top 1b which can move along the body axis direction (the longitudinal direction of the table top 1b) of a patient P placed on it. The C-shaped arm 3 covers this bed 1 sideways. The CT gantry 2 has a hollow portion H into which the table top 1b can be inserted.

As shown in FIG. 1, the bed 1 is made up of a stand 1a which can ascend and descend along an arrow C, and the table top 1b which is supported on this stand 1a so as to be movable along the longitudinal direction (an arrow D). To enlarge the access space for a doctor (operator) with respect to an object to be examined, the table top 1b is cantilevered by the stand 1a fixed on the floor surface.

The X-ray CT apparatus includes, e.g., a display device 2a and an image reconstructing device (computer device), in addition to the CT gantry 2 described above. This CT gantry 2 includes a projection data acquisition system which comprises an X-ray tube and an X-ray detector. The X-ray detector is connected to the image reconstructing device. On the basis of an output from this X-ray detector, the image reconstructing device reconstructs tomographic image data pertaining to the patient P. The display device 2a displays the reconstructed tomographic image.

The CT gantry 2 is placed on a pair of rails 22 which run on the floor surface along the longitudinal direction (an arrow A) of the table top 1b, such that this CT gantry 2 can move back and forth and can tilt along an arrow B. Each rail 22 has a length by which its one end reaches the stand 1a of the catheter bed 1, and its other end reaches a position separated a predetermined distance from the catheter bed 1. The CT gantry 2 runs by itself by a power source installed in this CT gantry 2. The CT gantry 2 can tilt within the range of ±30°. This makes it possible to acquire obliquely cut X-ray tomographic images of the patient P.

Figure 4:
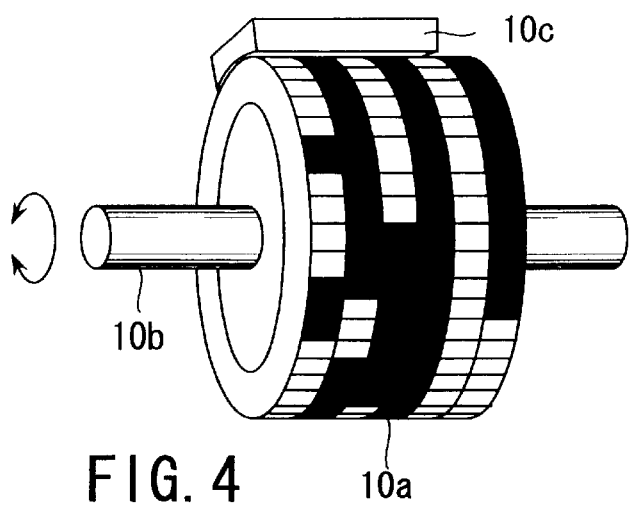
FIG. 4 is a perspective view showing the structure of an absolute encoder for position detection in the embodiment.

In addition, the CT gantry 2 includes a pair of absolute encoders (position detecting means) 10 to detect the front and rear positions. As shown in FIG. 4, for example, this encoder 10 comprises a rotor 10a on the surface of which a magnetic scale is previously formed, a shaft 10b extending through the center of this rotor 10a, and a detecting head 10c placed along the surface of the rotor 10a. The "movement (arrow A)" of the CT gantry 2 is converted into a "rotation" by, e.g., a rack and pinion, and this rotates the shaft 10b. An output signal corresponding to the pattern of the magnetic scale previously formed on the rotor 10a is acquired from the detecting head 10c. That is, the position of the CT gantry 2 is detected on the basis of the output from the encoder 10.

Typically, the position is defined on an XYZ coordinate system in which the center of the catheter bed 1 is the origin.

The position of the CT gantry 2 read by the encoder 10 is held even after the power supply of the IVR-CT apparatus main body is shut down. That is, although the rotation of the rotor 10a stops when the power supply is shut down, this stopped state gives rise to the state in which a certain predetermined magnetic scale pattern faces the detecting head 10c. This makes "stop of the rotor 10a" equivalent to "holding the absolute coordinate values". In this embodiment, therefore, the values immediately before power supply shutdown are used as the absolute coordinate values when the power supply is turned on.

Furthermore, although the magnetic encoder 10 is explained as an example, the present invention is not limited to this form. For example, a brush encoder or photoelectric encoder can also be used as well as a magnetic encoder. Also, the type of rotary encoder or linear encoder does not matter provided that the encoder can appropriately express an operation amount corresponding to the translational motion of the CT gantry 2.

A plurality of encoders having the same structure as this encoder 10 are set in a plurality of movable portions, in order to detect the tilt angle of the CT gantry 2, the height and position of the table top 1b, and the positions of all other movable portions.

An X-ray tube 6 is mounted on one end of the C-shaped arm 3, and an X-ray detector 5 comprising an image intensifier (I.I.), an optical system, and a TV camera is mounted on the other end. This X-ray detector 5 is supported to be movable in the direction of an arrow J, i.e., to come close to and move away from an iso center IS. A distance SID between the X-ray tube 6 and the X-ray detector 5 can be adjusted by the movement of the X-ray detector 5.

In addition to the C-shaped arm 3, the X-ray tube 6, and the X-ray detector 5 described above, the X-ray diagnostic apparatus 4 has an image reconstructing device (not shown) connected to the X-ray detector 5, a display device 4a, and the like. In this X-ray diagnostic apparatus 4 having these components, while a doctor is performing an operation or examination, e.g., inserting a catheter into the patient P, X-ray imaging can be performed by angiography at the same time.

The C-shaped arm 3 is supported by an arm holder 3b so as to be slidably rotatable (in the direction of an arrow G) around a horizontal rotation axis (called a second horizontal rotation axis) passing the iso center IS. This arm holder 3b is supported by an outside arm 3a so as to be tiltable (in the direction of an arrow F) around a first horizontal rotation axis passing the iso center IS and perpendicular to the second horizontal rotation axis. This outside arm 3a is supported by an arm base 3c so as to be rotatable (in the direction of an arrow E) around a vertical rotation axis passing the iso center IS.

The arm base 3c is fitted on a pair of longitudinal rails 3d so that this arm base 3c can move along the longitudinal direction (an arrow I) of the table top 1b. The longitudinal rails 3d are fitted on a pair of lateral rails 3e fixed to the ceiling, such that these longitudinal rails 3d can move along the lateral direction (an arrow H) of the table top 1b. The length of the lateral rails 3e is longer than the width of the CT gantry 2. Hence, the C-shaped arm 3 can move in the lateral direction to a position where this C-shaped arm 3 does not interfere with the CT gantry 2, and can park at this position.

A table side control panel 50b is mounted together with an LCD display panel 50a on the upper side surface of the stand 1a of the bed 1.

Figure 5B:
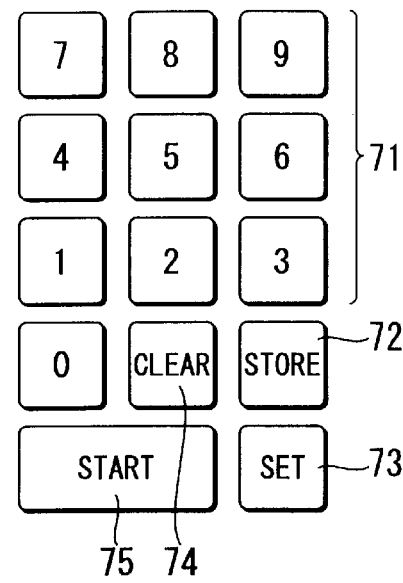
FIG. 5B is a detailed view of positioning switches shown in FIG. 5A.
Figure 5A:
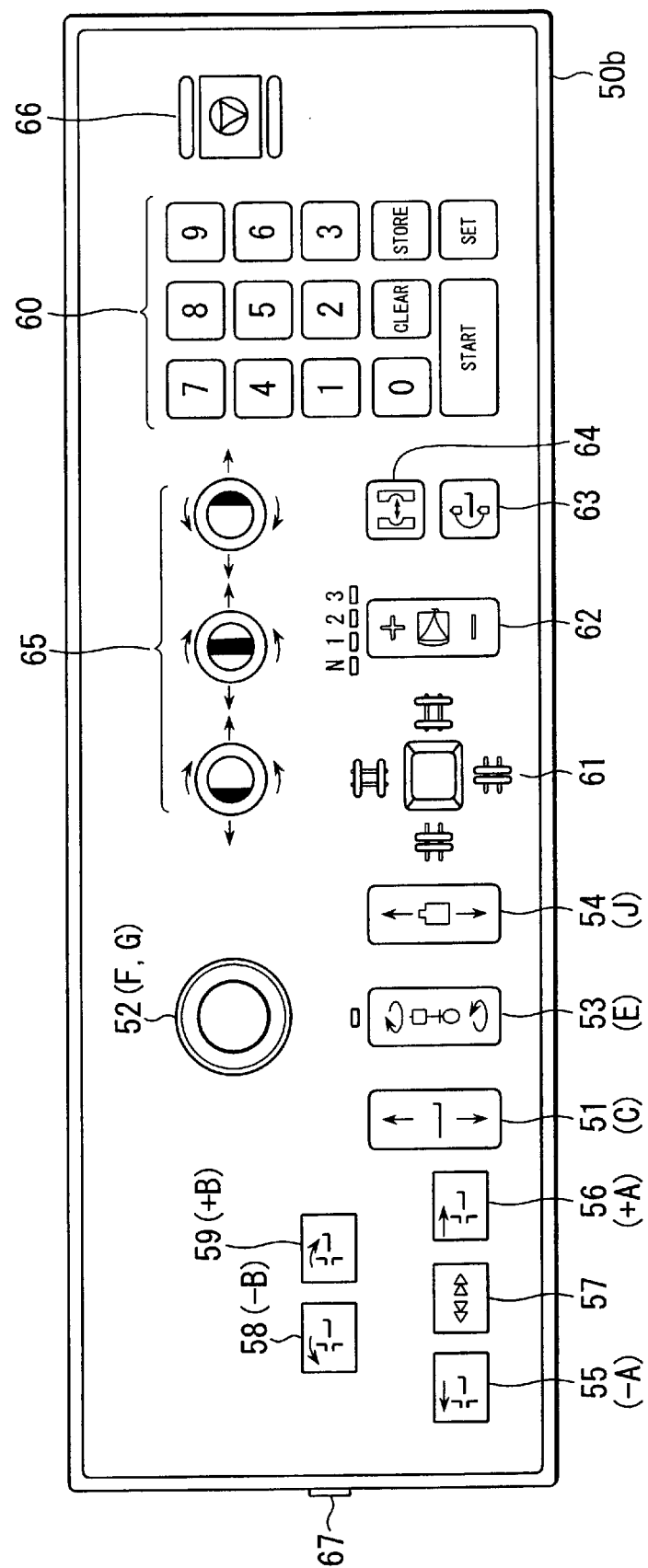
FIG. 5A is a plan view of a table side control panel shown in FIG. 1.

As shown in FIG. 5A, the control panel 50b includes a manual control switch 51 for the up/down movement (arrow C) of the table top 1b of the bed 1, a manual control stick 52 for the tilt rotation (F) and the slide rotation (G) of the C-shaped arm 3, a manual control switch 53 for the strut rotation (E) of the C-shaped arm 3, and a manual control switch 54 for the front/rear movement (I) of the detector 5.

In addition, this control panel 50b includes manual control switches 55 and 56 for the front/rear motion (A) of the CT gantry 2, manual operation switches 58 and 59 for the tilt (B) of the CT gantry 2, and switches 60 pertaining to auto positioning. When an operator presses the manual control switch 55 or 56 while holding down a rapid switch 57, the forward or backward movement of the CT gantry 2 is accelerated. As shown in FIG. 5B, the auto positioning switches 60 include set keys (ten keys) 71, a store key 72, an auto set key 73, a cancel key 74, and an auto positioning start key 75.

Furthermore, the control panel 50b has a square aperture blade control switch 61, an X-ray image size switch 62, a clinical angle control select switch 63, a security filter right-and-left change switch 64, a security filter control switch 65, an emergency stop switch 66, and an interlock release switch 67.

The table side control panel 50b does not include control switches pertaining to the side movement (H) and the longitudinal movement (I) of the C-shaped arm 3. However, manual control switches, including these switches, concerning all movements (E–J) of the C-shaped arm 3 are provided on a C-shaped arm control panel 8 mounted on the outside arm 3a of the C-shaped arm 3. Movements (E, F, G, and J) except for the side movement (H) and the longitudinal movement (I) of the C-shaped arm 3 can be manually controlled by using either the table side control panel 50b or the C-shaped arm control panel 8. For the sake of safety, the side movement (H) and the longitudinal movement (I) of the C-shaped arm 3 can be manually controlled by using the C-shaped control panel 8, not from the table side control panel 50b.

Figure 6:
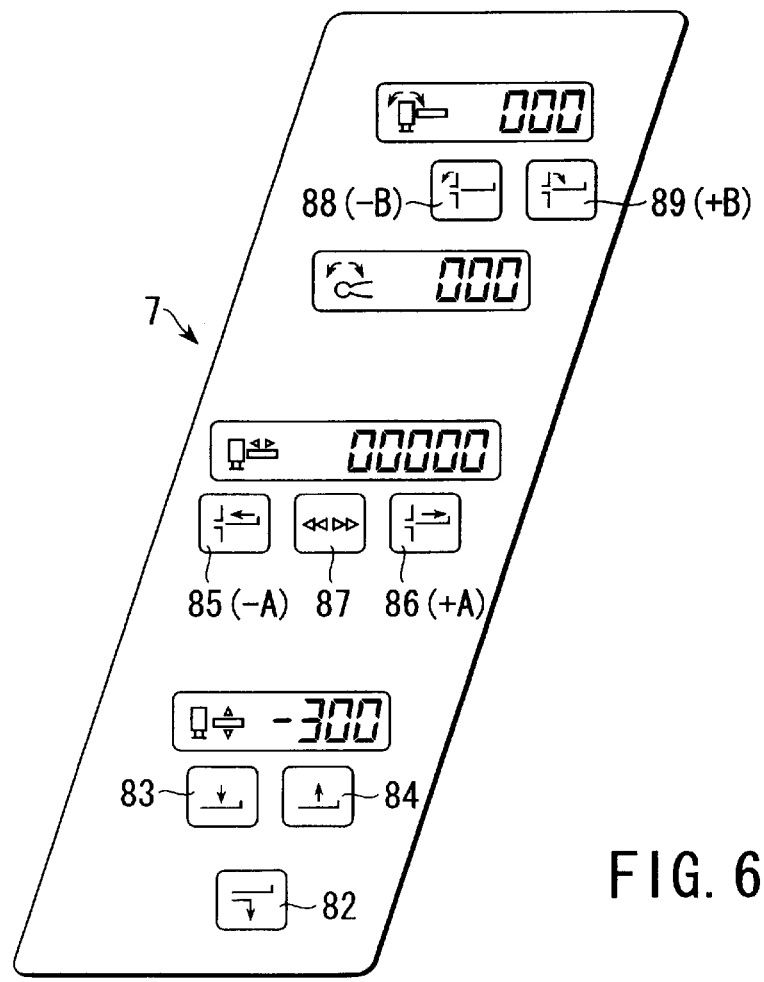
FIG. 6 is a plan view of a CT gantry control panel shown in FIG. 1.

FIG. 6 shows a CT gantry control panel 7 mounted on the CT gantry 2. This CT gantry control panel 7 includes manual control switches 85 and 86 for the front/rear movement (A) of the CT gantry 2, manual control switches 88 and 89 for the tilt (B) of the CT gantry 2, and a rapid switch 87, along with manual control switches 83 and 84 for the up/down movement (arrow C) of the table top 1b of the bed 1, and a manual control switch 82 for the lowermost movement of the table top 1b of the bed 1. The front/rear movement (A) and the tilt (B) of the CT gantry 2 can be manually controlled by using either the CT gantry control panel 7 and the table side control panel 50b. Also, the up/down movement (arrow C) of the table top 1b can be manually controlled by using either the CT gantry control panel 7 and the table side control panel 50b.

Figure 7:
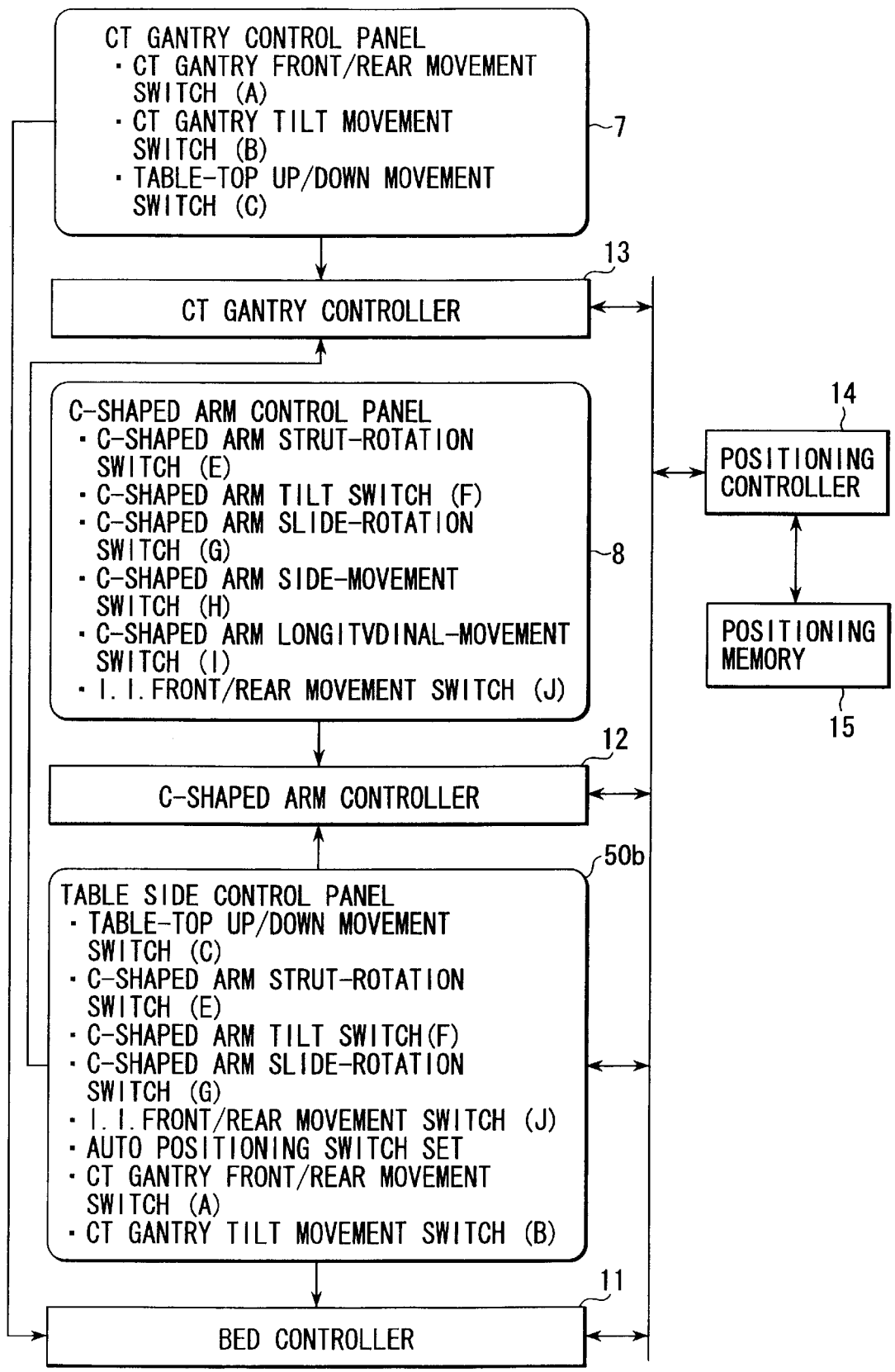
FIG. 7 is a view showing the configuration of an operation control system of the embodiment.

FIG. 7 shows the configuration of an operation control system of the IVR-CT apparatus of this embodiment. A bed controller 11 is configured to control the up/down movement (C) and the longitudinal movement (D) of the table top 1b. A C-shaped arm controller 12 is configured to control the movements (E–J) of the C-shaped arm 3. A CT gantry controller 13 is configured to control the movements (A and B) of the CT gantry 2. In an auto positioning mode, these controllers 11, 12, and 13 are placed under the control of an auto positioning controller 14. In a manual control mode, these controllers 11, 12, and 13 drive movable parts in accordance with the manual control amounts. A positioning memory 15 for storing a plurality of positioning data sets is connected to the positioning controller 14. A plurality of positioning data sets are registered in this positioning memory 15. These positioning data sets include position data of the table top 1b, position data of the C-shaped arm 3, and position data of the CT gantry 2, and these position data are managed by position numbers unique to the data. Auto positioning is realized by control by the auto positioning controller 14 on the basis of the position data contained in the position data sets.

The position data set registration process and the auto positioning process controlled by the auto positioning controller 14 will be described below.

Figure 8A:
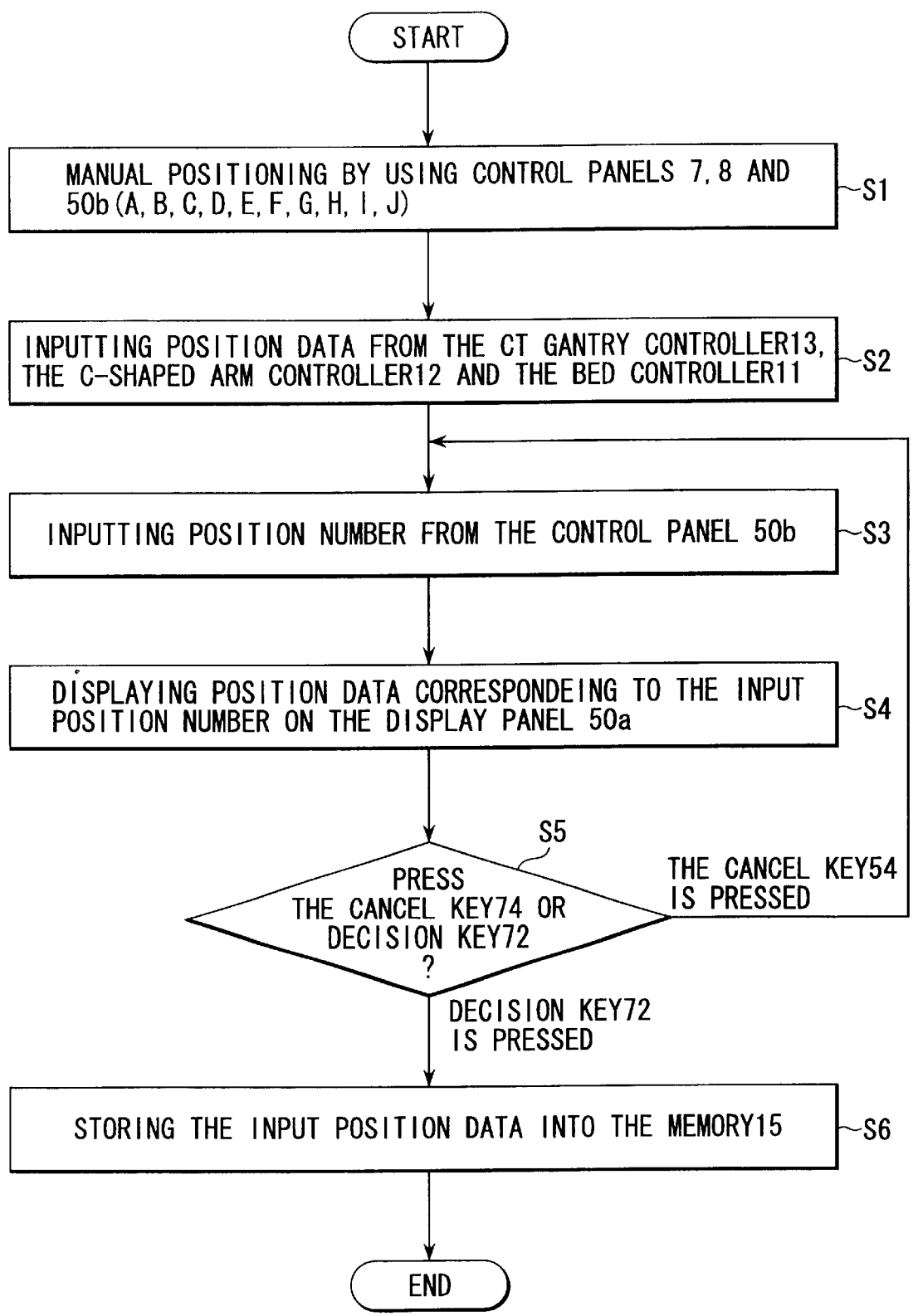
FIG. 8A is a flow chart of a position registration procedure performed by an auto positioning controller shown in FIG. 7.

FIG. 8A shows the flow of the position data set registration process performed by the auto positioning controller 14. In step S1, an operator operates the manual control switches of the control panel 50b to set the height C of the table top 1b to an arbitrary value. The operator also operates the manual control switches of the control panel 8 and/or the control panel 50b to set a strut-rotation angle E, a tilt-rotation angle F, a slide-rotation angle G, a lateral position H, and a longitudinal position I of the C-shaped arm 3 and a front/rear position J of the detector 5 to arbitrary values. Additionally, the operator operates the manual control switches of the control panel 7 or 50b to set a front/rear position A and a tilt angle B of the CT gantry 2 to arbitrary values.

In step S2, the bed controller 11, the C-shaped arm controller 12, and the CT gantry controller 13 supply position data read out via the encoders to the auto positioning controller 14. Also, the data of a position number input from the control panel 50b by the operator is supplied from the control panel 50b to the auto positioning controller 14 (S3). The auto positioning controller 14 displays position data corresponding to the supplied position number on the display panel 50a (S4).

If the input position number already manages another position data set, i.e., if a position data set corresponding to the input position number is already registered in the memory 15, this already registered position data is displayed.

On the other hand, if the input position number does not manage any other position data set, i.e., if the input position number is unused and no position data set corresponding to the input position number is registered in the memory 15, the position data supplied from the bed controller 11, the C-shaped arm controller 12, and the CT gantry controller 13 in step S2 is displayed.

The operator checks the displayed position and presses the cancel key 74 or the store key 72 (S5). If the cancel key 74 is pressed, the flow returns to step S3 to prompt the operator to again input a position number. If the store key 72 is pressed, the position data set supplied from the bed controller 11, the C-shaped arm controller 12, and the CT gantry controller 13 is related to the input position number and written in the memory 15 (S6).

A desired positional relationship is determined in accordance with a "portion to be imaged of the patient P". Examples are CT imaging of the "head" of the patient P, and X-ray imaging of the "abdomen" of the patient P by the use of the C-shaped arm 3. Also, in examination using the CT gantry 2 and the C-shaped arm 3 in cooperation with each other, desired positional relationships are determined following the operation procedure. For example, imaging is first performed using the C-shaped arm 3 and then performed using the CT gantry 2. When a plurality of desired positional relationships are thus present, the above operation is repeated until all these positional relationships are completely stored in the positioning memory. As described above, it is possible to actually set the C-shaped arm 3 and the CT gantry 2 in desired positions at desired angles, and register the corresponding position data set.

Position numbers are prepared from 0 to 99. For example, 93 position numbers from 4 to 9 and 13 to 99 are assigned for a user to register position data sets. The remaining seven position numbers from 1 to 3 and 10 to 12 are used by the manufacturer to manage initially prepared position data sets.

Representative examples of the position data sets initially registered by the manufacturer are a head standard position data set, an abdomen standard position data set, and a park position data set. For example, the head standard position data set contains a C-shaped arm 3 strut-rotation angle of 90°, a C-shaped arm 3 tilt angle of 0°, a C-shaped arm 3 slide-rotation angle of 0°, a C-shaped arm 3 longitudinal position of 350 mm, a C-shaped arm 3 side position of 0 mm, a table top 1b height of 1,000 mm, and the head position of a patient of a standard physique as the front/rear position of the CT gantry 2. Likewise, the abdomen standard position data set contains a C-shaped arm 3 strut-rotation angle of 90°, a C-shaped arm 3 tilt angle of 0°, a C-shaped arm 3 slide-rotation angle of 0°, a C-shaped arm 3 longitudinal position of 800 mm, a C-shaped arm 3 side position of 0 mm, a table top 1b height of 1,000 mm, and the abdomen position of a patient of a standard physique as the front/rear position of the CT gantry 2.

The park position data set contains park position data of the C-shaped arm 3 separated from the catheter bed 1, and park position data of the CT gantry 2. The park position data of the C-shaped arm 3 contains data necessary to set the C-shaped arm 3 in a position separated a predetermined distance from the side of the bed 1, such that the tilt-rotation axis of the C-shaped arm 3 is substantially parallel to the longitudinal axis of the table top 1b. The park position data of the CT gantry 2 contains data necessary to place the CT gantry 2 in the rearmost position of the front/rear movement.

Figure 8B:
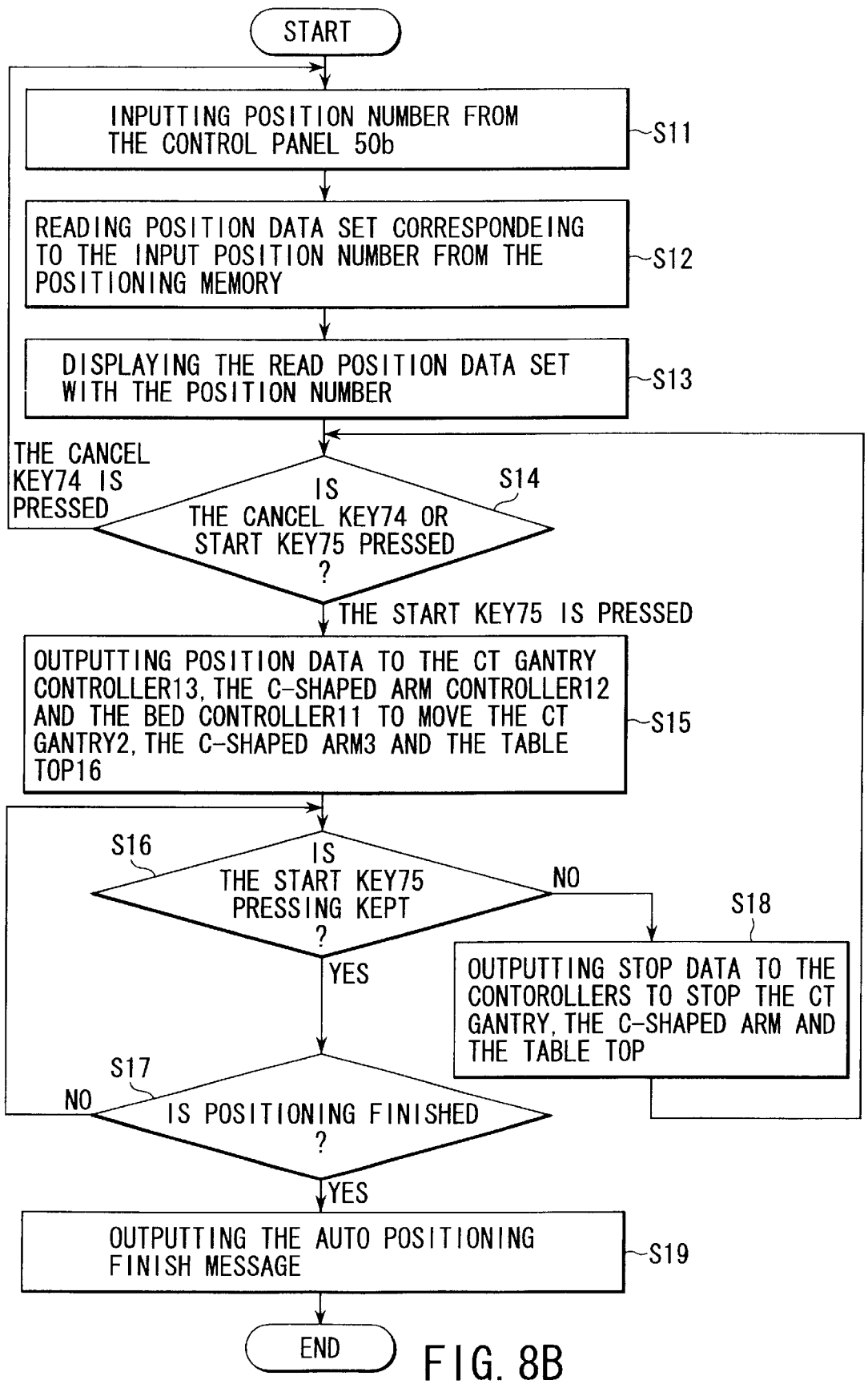
FIG. 8B is a flow chart of an auto positioning procedure performed by the auto positioning controller shown in FIG. 7.

The auto positioning process will be described next. FIG. 8B shows the procedure of the auto positioning process performed by the auto positioning controller 14. First, a given position number is input via the control panel 50b (S11). The auto positioning controller 14 reads out a position data set corresponding to the input position number from the memory 15 (S12). As shown in FIGS. 9A to 9D, the auto positioning controller 14 causes the display panel 50a to display this position data set together with the initially registered position data set or the input position number (S13).

The operator checks the displayed position data and presses the cancel key 74 or the start key 75 (S14). If the cancel key 74 is pressed, the flow returns to step S11 to prompt the operator to again input a position number.

If the start key 75 is pressed, the auto positioning controller 14 outputs the corresponding position data to the bed controller 11, the C-shaped arm controller 12, and the CT gantry controller 13 (S15). In accordance with this position data, the bed controller 11, the C-shaped arm controller 12, and the CT gantry controller 13 control the movements of the table top 1b, the C-shaped arm 3, and the CT gantry 2, respectively.

For the sake of safety, the table top 1b, the C-shaped arm 3, and the CT gantry 2 are moved only during a period in which the operator keeps pressing the start key 75. That is, the auto positioning controller 14 checks in step S16 whether the start key 75 remains pressed. If the operator releases the start key 75, the auto positioning controller 14 outputs stop data to the bed controller 11, the C-shaped arm controller 12, and the CT gantry controller 13 (S18). Upon receiving this stop data, the bed controller 11, the C-shaped arm controller 12, and the CT gantry controller 13 stop the movements of the table top 1b, the C-shaped arm 3, and the CT gantry 2, respectively. Accordingly, if a dangerous situation such as collision is pressing when the operator is visually checking the movements of the table top 1b, the C-shaped arm 3, and the CT gantry 2, he or she can urgently stop the movements of the table top 1b, the C-shaped arm 3, and the CT gantry 2 only by releasing the start key 75.

While the operator is holding down the start key 75, i.e., while no stop data is input, the bed controller 11, the C-shaped arm controller 12, and the CT gantry controller 13 keep moving the table top 1b, the C-shaped arm 3, and the CT gantry 2 until they reach the positions corresponding to the position data (S17). Whether these members have reached their respective positions is checked by comparing the current positions detected by the encoders with the positions (target positions) indicated by the position data.

When the table top 1b, the C-shaped arm 3, and the CT gantry 2 have reached their target positions, the bed controller 11, the C-shaped arm controller 12, and the CT gantry controller 13 stop their movements and output positioning finish notification to the auto positioning controller 14. When receiving the positioning finish notification from all of the bed controller 11, the C-shaped arm controller 12, and the CT gantry controller 13, the auto positioning controller 14 outputs an auto positioning finish message (S19). This auto positioning finish message is output by generating a finish buzzer, generating a voice, or displaying characters.

The C-shaped arm 3 and the CT gantry 2 may interfere with each other depending on the positional relationship between the current positions of the C-shaped arm 3 and the CT gantry 2 and the target positions. In this case, the auto positioning controller 14 once retracts one of the C-shaped arm 3 and the CT gantry 2, e.g., the CT gantry 2, to the park position, moves the C-shaped arm 3 to the target position, and then moves the CT gantry 2 from the park position to the target position. Alternatively, the auto positioning controller 14 once retracts the C-shaped arm 3 to the park position, moves the CT gantry 2 to the target position, and then moves the C-shaped arm 3 from the park position to the target position.

The movement sequence of the C-shaped arm 3 and the CT gantry 2 is calculated by the auto positioning controller 14. This movement sequence can be calculated before a position data set is registered, and contained together with position data in the position data set. Alternatively, the movement sequence is calculated, after a position data set is read out, from the target positions and the current positions.

Details of the park positioning will be described next. As described above, the park position of the C-shaped arm 3 is the position separated a predetermined distance from the side of the bed 1, at which the tilt-rotation axis of the C-shaped arm 3 is substantially parallel to the longitudinal axis of the table top 1b. This park position of the C-shaped arm 3 is accomplished because the length of the side rails 3e of the C-shaped arm 3 is designed to be longer than the width of the CT gantry 2. This contributes to the realization of all of the following: the installation area of this IVR-CT apparatus is reduced, the movement to the park position is completed within a short time period, and the movement path of the CT gantry 2 is not interfered with.

Figure 10A:
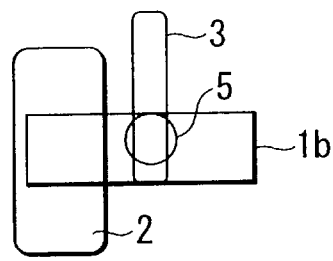
FIGS. 10A to 10E are plan views showing the movements of park positioning performed by the auto positioning controller shown in FIG. 7.
Figure 10B:
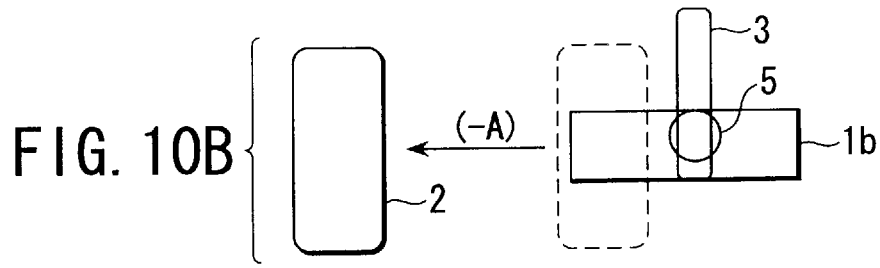
Figure 10C:
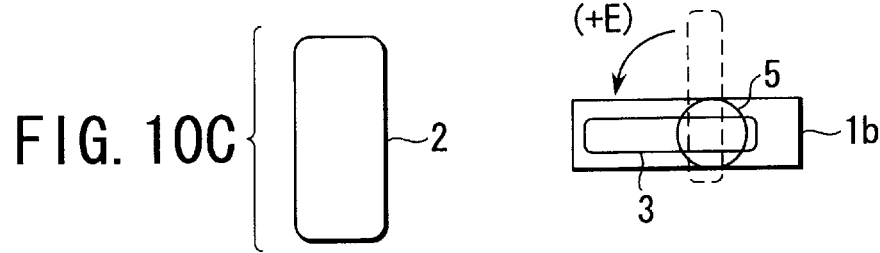
Figure 10D:
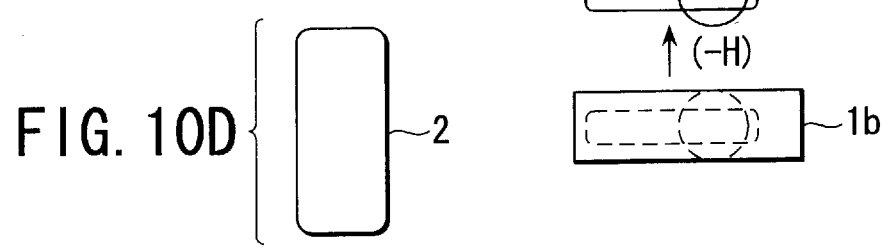

FIGS. 10A to 10E illustrate the movement sequence of the C-shaped arm 3 and the CT gantry 2 in the park positioning process performed by the auto positioning controller 14. Assume, as shown in FIG. 10A, that the C-shaped arm 3 is initially in the most typical state in which the C-shaped arm 3 extends across substantially the center of the table top 1b in front of the CT gantry 2, and the rear end portion of the table top 1b is inserted into the hollow of the CT gantry 2. In this state, an operator inputs a position number corresponding to the park position data set and presses the start key 75 to execute the park positioning. First, as shown in FIG. 10B, the CT gantry 2 moves to the rearmost position (park position). The C-shaped arm 3 then moves sideways (H) as shown in FIG. 10C, along with a strut rotation (E) of 90° shown in FIG. 10C. Although the side movement of the C-shaped arm 3 is typically performed in parallel with the strut rotation, it can also be performed after the strut rotation is completed.

Figure 10E:
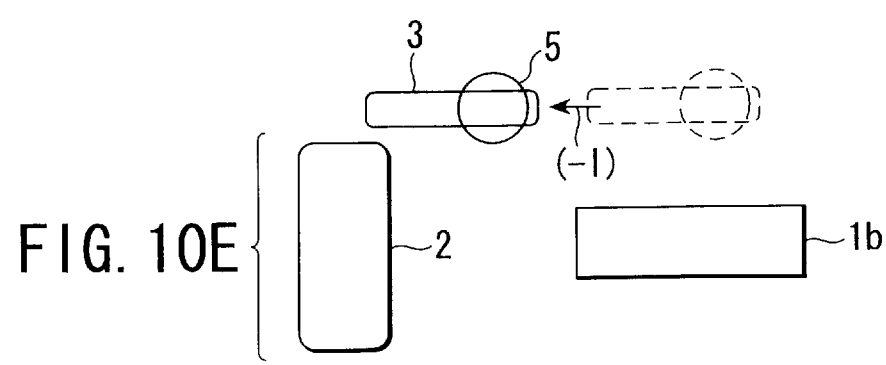

Finally, as shown in FIG. 10E, the C-shaped arm 3 is moved in the longitudinal direction. However, this longitudinal movement can also be omitted.

In this embodiment as described above, the only operations substantially need to be performed by an operator of the apparatus are to input a position number and press the start key 75. After that, the bed 1, the CT gantry 2, and the C-shaped arm 3 are automatically positioned under the control of the auto positioning controller 14. That is, when CT examination is to be carried out after X-ray examination is performed by the X-ray diagnostic apparatus 4 in the conventional apparatus, an operator must move away from the bed 1 to operate the control panel 7 of the CT gantry 2. In contrast, in this embodiment an operator of the apparatus can set a desired positional relationship between the bed 1, the CT gantry 2, and the C-shaped arm 3 only by simple button pressing on the control panel 50b at the side of the bed 1, regardless of a portion to be imaged of the patient P, the type of examination such as the simultaneous use of the X-ray CT apparatus and the X-ray diagnostic apparatus 4, or the examination procedure. This means that the operability of the IVR-CT apparatus of this embodiment is especially improved compared to that of the conventional apparatus.

Figure 11:
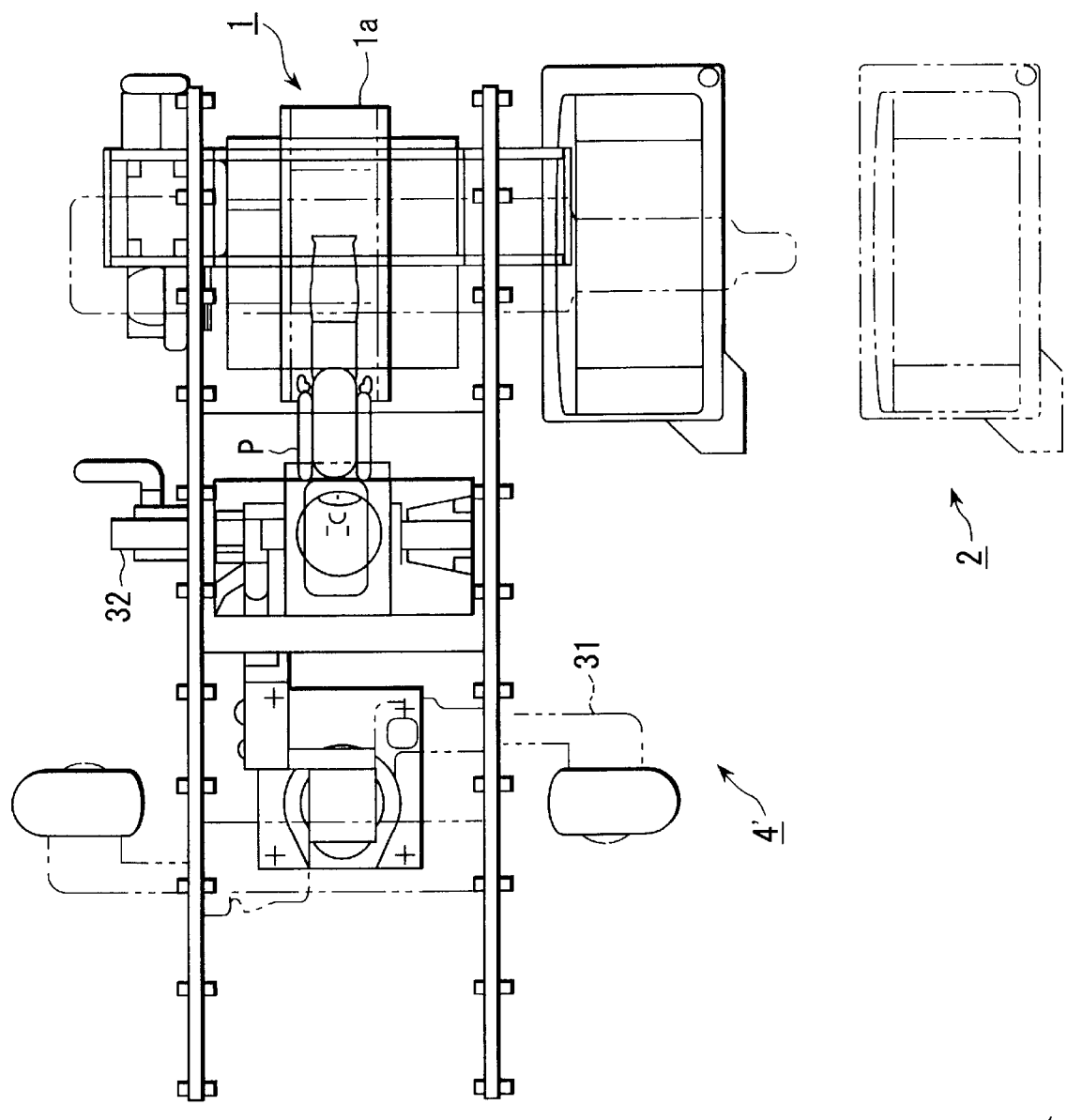
FIG. 11 is a plan view of an IVR-CT apparatus as a modification of the embodiment.
Figure 12:
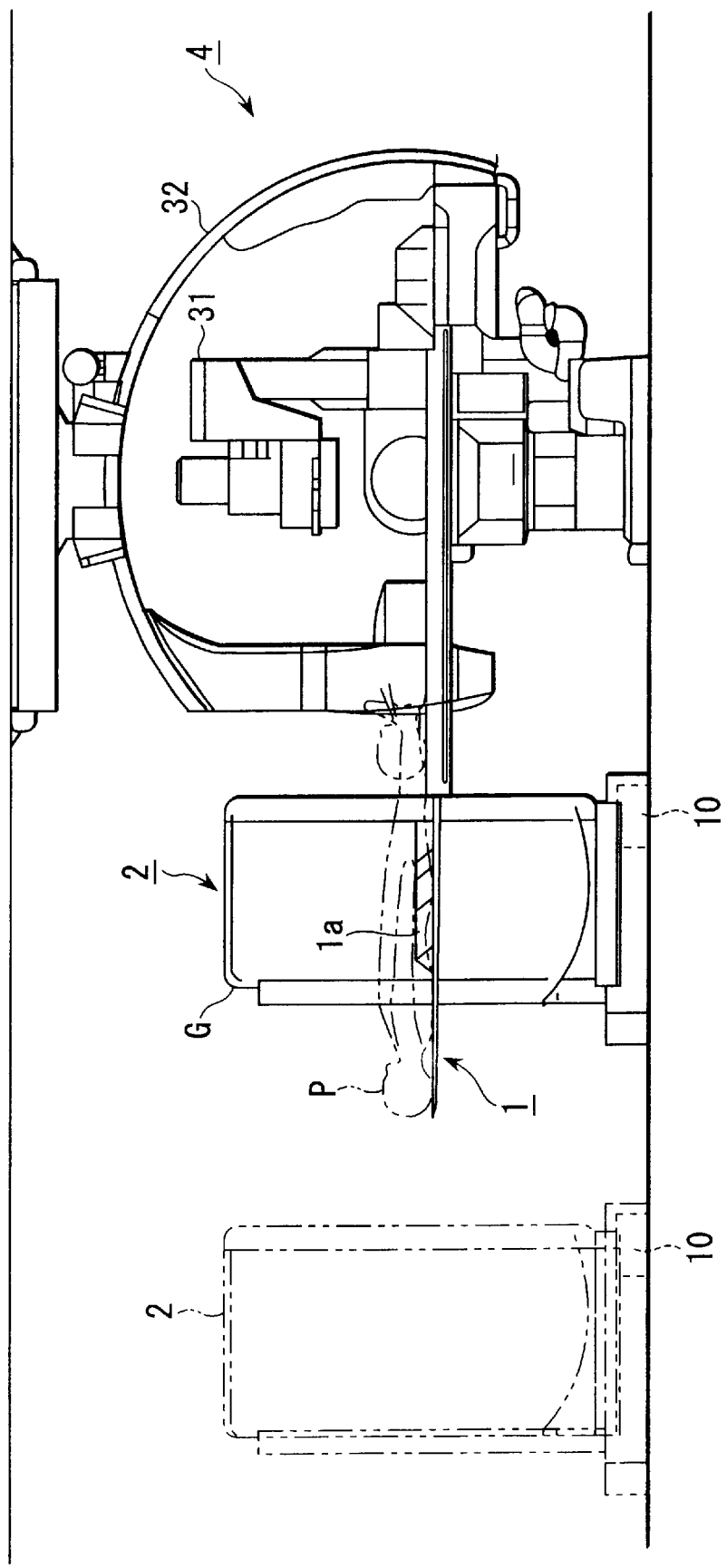
FIG. 12 is a side view of the IVR-CT apparatus shown in FIG. 11.

In the IVR-CT apparatus of the above embodiment, the X-ray diagnostic apparatus 4 has only one C-shaped arm 3. However, the present invention is also applicable to an IVR-CT apparatus so-called "biplane system" having two or more C-shaped arms 3. For example, this biplane system has an arrangement as shown in FIGS. 11 and 12. This IVR-CT apparatus shown in FIGS. 11 and 12 includes one X-ray CT apparatus having a CT gantry 2 similar to FIGS. 1 to 3, but a biplane system 4' has two C-shaped arms 31 and 32. However, the construction of these C-shaped arms 31 and 32 is not largely different from the construction of the C-shaped arm 3 described above. Also, as shown in FIG. 11, a bed 1 of this system can rotate such that the surface of a table top 1b stays parallel to the floor surface. Accordingly, it is possible not only to insert the bed 1 into the CT gantry 2 but also to set the direction of the bed 1 (or a patient P) to be perpendicular to that positioning. Even in a case like this, the auto positioning process is naturally applicable. Therefore, it is not difficult to apply the description concerning the above embodiment to this biplane system such that the description is in conformity with the system, so a practical embodiment of the system can be easily reached.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. An IVR-CT apparatus comprising:
a bed including a table top movable in a longitudinal direction thereof;
an X-ray diagnostic apparatus including an arm movably placed in the vicinity of said bed;
an X-ray CT apparatus including a CT gantry movably placed in the vicinity of said bed;
a position memory for storing a plurality of position data sets containing position data of the arm and position data of said CT gantry;
a control panel including a plurality of positioning switches for selecting an arbitrary one of the plurality of position data sets; and
a controller configured to control the movements of the arm and the movements of said CT gantry in accordance with the selected position data set.

2. An apparatus according to claim 1, wherein said control panel is mounted on said bed.

3. An apparatus according to claim 1, wherein said bed is a catheter bed.

4. An apparatus according to claim 1, wherein said control panel includes a plurality of manual control switches for said table top and a plurality of manual control switches for the arm, in addition to said plurality of positioning switches.

5. An apparatus according to claim 1, wherein said control panel includes a plurality of manual control switches for said table top, a plurality of manual control switches for the arm, and a plurality of manual control switches for said CT gantry, in addition to said plurality of positioning switches.

6. An apparatus according to claim 1, further comprising:
an arm control panel mounted on the arm and including a plurality of manual control switches for the arm; and
a CT gantry control panel mounted on said CT gantry and including a plurality of manual control switches for said CT gantry.

7. An apparatus according to claim 1, further comprising a display panel for displaying the position data of the arm and the position data of said CT gantry.

8. An apparatus according to claim 7, wherein said display panel is mounted with said control panel on said bed.

9. An apparatus according to claim 1, wherein said X-ray diagnostic apparatus includes a plurality of longitudinal-movement rails for supporting the arm such that the arm can move along the longitudinal direction of said table top, and a side-movement rail for supporting said plurality of longitudinal-movement rails such that said plurality of longitudinal-movement rails can move along the lateral direction of said table top, the length of said side-movement rail being longer than the width of said CT gantry.

10. An apparatus according to claim 1, wherein the plurality of position data sets contain sequence data which indicates the movements of the arm and the movements of said CT gantry to avoid mutual interference, in addition to the position data of the arm and the position data of said CT gantry.

11. An apparatus according to claim 1, wherein
the plurality of position data sets have a park position data set containing sequence data which indicates the movements of the arm and the movements of said CT gantry to avoid mutual interference, in addition to the position data of the arm and the position data of said CT gantry, and
in accordance with the sequence data, said CT gantry moves to a position most separated from said bed in the longitudinal direction of said table top, and the arm moves along the lateral direction of said table top together with strut rotation after the movement of said CT gantry is completed, under the control of said controller.

12. An apparatus according to claim 11, wherein the arm is parked in a position separated a predetermined distance from the side of said bed with the tilt-rotation axis of the arm substantially parallel to the longitudinal axis of said table top.

13. An IVR-CT apparatus comprising:

a bed including a table top movable in a longitudinal direction thereof;

an X-ray diagnostic apparatus including an X-ray video system, an arm for mounting said X-ray video system, a mechanism for supporting the arm such that the arm can move along the longitudinal direction of said table top, a mechanism for supporting the arm such that the arm can move along the lateral direction of said table top, a mechanism for supporting the arm such that the arm can rotate around a vertical axis, a mechanism for supporting the arm such that the arm can tilt around a first horizontal axis, and a mechanism for supporting the arm such that the arm can rotate clockwise and counterclockwise around a second horizontal axis;

an X-ray CT apparatus including an X-ray projection data acquisition system, a CT gantry having said X-ray projection data acquisition system, and a mechanism for supporting said CT gantry such that said CT gantry can move along the longitudinal direction of said table top; and a controller for controlling the movement of the arm to an arm park position and the movement of said CT gantry to a CT gantry park position, wherein under the control of said controller, said CT gantry moves to the CT gantry park position most separated from said bed in the longitudinal direction of said table top, and, after the movement of said CT gantry is completed, the arm moves along the lateral direction of said table top together with strut rotation and is parked in a position separated a predetermined distance from the side of said bed with the tilt-rotation axis of the arm substantially parallel to the longitudinal axis of said table top.

14. An IVR-CT apparatus comprising:

a bed including a table top movable in a longitudinal direction thereof;

an X-ray diagnostic apparatus including an arm movably placed in the vicinity of said bed;

an X-ray CT apparatus including a CT gantry movably placed in the vicinity of said bed;

an arm control panel mounted on the arm and having a manual control function of the arm;

a CT gantry control panel mounted on said CT gantry and having a manual control function of said CT gantry; and a table side control panel mounted on said bed and having a manual control function of said bed in addition to the manual control function of the arm and the manual control function of said CT gantry.

15. An IVR-CT apparatus comprising:

a bed including a table top movable in a longitudinal direction thereof;

an X-ray diagnostic apparatus including an arm movably placed in the vicinity of said bed; and an X-ray CT apparatus including a CT gantry movably placed in the vicinity of said bed, wherein said X-ray diagnostic apparatus includes a plurality of longitudinal-movement rails for supporting the arm such that the arm can move along the longitudinal direction of said table top, and a side-movement rail for supporting said plurality of longitudinal-movement rails such that said plurality of longitudinal-movement rails can move along the lateral direction of said table top, the length of said side-movement rail being longer than the width of said CT gantry.

\* \* \* \* \*